United States Patent [19]

Roscher

[11] Patent Number: 5,391,815
[45] Date of Patent: Feb. 21, 1995

[54] METHOD OF SEPARATING VINYLPHOSPHONIC ACID FROM CRUDE MIXTURES

[75] Inventor: Günter Roscher, Kelkheim, Germany

[73] Assignee: Hoechst Aktiengesellschaft, Frankfurt am Main, Germany

[21] Appl. No.: 978,702

[22] PCT Filed: Jul. 27, 1991

[86] PCT No.: PCT/EP91/01412
§ 371 Date: Feb. 3, 1993
§ 102(e) Date: Feb. 3, 1993

[87] PCT Pub. No.: WO92/02524
PCT Pub. Date: Feb. 20, 1992

[30] Foreign Application Priority Data

Aug. 4, 1990 [DE] Germany ............... 40 24 828.3

[51] Int. Cl.$^6$ .............................................. C07F 9/38
[52] U.S. Cl. ...................................................... 562/8
[58] Field of Search ........................................... 562/8

[56] References Cited

U.S. PATENT DOCUMENTS

| | | | |
|---|---|---|---|
| 3,896,163 | 7/1975 | Jacques | 562/25 |
| 4,585,636 | 4/1986 | Iosef et al. | 423/321 |
| 4,739,092 | 4/1988 | Nozaki et al. | 558/150 |

*Primary Examiner*—José G. Dees
*Assistant Examiner*—Joseph M. Conrad

[57] ABSTRACT

Method of separating vinylphosphonic acid from crude mixtures.

The invention relates to a method for separating vinylphosphonic acid from crude mixtures, the separation being carried out by extraction with alcohols and/or ketones, which in each case comprise at least 5 carbon atoms.

According to the invention, vinylphosphonic acid can be obtained in high purity and good yield from highly contaminated crude mixtures.

18 Claims, 1 Drawing Sheet

METHOD OF SEPARATING VINYLPHOSPHONIC ACID FROM CRUDE MIXTURES

DESCRIPTION

Various methods are known for the preparation of pure vinylphosphonic acid. Thus, for example, vinylphosphonyl dichloride can be hydrolyzed. However, the synthesis of pure vinylphosphonyl chloride is technically laborious. A number of other methods for the preparation of pure vinylphosphonic acid have therefore already been described in the literature.

Thus, a bottom mixture which comprises in total up to 85% of diverse vinylphosphonic acid derivatives is obtained on thermal decomposition of dialkyl acetoxyethanephosphonates in accordance with German Offenlegungsschrift 3 001 894, alkyl acetates and dialkyl ethers being split off. An up to 82% strength vinylphosphonic acid is obtained on hydrolysis of this mixture, for example in accordance with German Offenlegungsschrift 3 110 975. However, this degree of purity is not sufficient for many applications of vinylphosphonic acid since, in general, degrees of purity of about 90–95% are desired and the phosphoric acid content should be less than 5% by weight.

According to the method described in German Offenlegungsschrift 3 120 437 for the preparation of pure vinylphosphonic acid, the bottom mixture obtained in accordance with the abovementioned German Offenlegungsschrift is subjected to thermal decomposition using orthocarboxylic acid esters, with the preparation of dialkyl vinylphosphonates, which, after distillation to give the pure product and hydrolysis, then give more highly concentrated vinylphosphonic acid. Trialkyl phosphate, which is virtually impossible to separate from the relevant dialkyl vinylphosphonate by distillation, is also always formed as a by-product of the vinylphosphonic acid preparation by this method. As a consequence, the vinylphosphonic acid obtained by hydrolysis of the relevant esters still contains at least 7% by weight of phosphoric acid. It is true that separation of the phosphoric acid in the form of magnesium ammonium hydrogen phosphate, which is sparingly soluble in water, is described in the literature, but this signifies a further additional step and gives rise to residual traces of magnesium ammonium salt in the vinylphosphonic acid, which traces interfere in some applications. Furthermore, the use of orthocarboxylic acid esters is economically expensive.

Pure vinylphosphonic acid can be obtained in accordance with German Offenlegungsschrift 3 707 149 by hydrolysis of a vinylphosphonic acid ester which has been obtained by vacuum cleavage of dialkyl acetoxyethanephosphonates. With this method also about 20% of a bottom material are obtained which still comprises diverse vinylphosphonic acid derivatives, which can be converted by thermal after-treatment and subsequent hydrolysis into a 50 to 70% strength vinylphosphonic acid, which must be regarded as lost if the vinylphosphonic acid contained in the mixture cannot be separated off.

The present invention now relates to a method for separating vinylphosphonic acid from crude mixtures, wherein the separation is effected by extraction with alcohols and/or ketones, which, in each case comprise at least 5 carbon atoms, preferably 5 to 15 carbon atoms and in particular 5 to 10 carbon atoms.

The alcohols used as extraction agent according to the invention are generally monohydric or dihydric, preferably monohydric; their hydrocarbon radical is preferably a branched or straight-chain aliphatic radical or a cycloaliphatic radical, which optionally can be substituted by $(C_1–C_4)$-alkyl groups, the number of which is generally 1 to 3. These radicals can optionally also comprise hetero atoms, such as oxygen atoms, or have groups which contain hetero atoms and are inert with respect to the crude mixture. Examples of such alcohols which may be mentioned here are: 2-ethylhexanol, cyclohexanol, the diverse heptanols, nonyl alcohol and the like. 2-ethylhexanol is in this case the preferred extraction agent.

The ketones which are similarly employed according to the invention as extraction agents have either two hydrocarbon radicals, preferably branched or straight-chain alkyl radicals, with, in total, the abovementioned number of carbon atoms, or they are derived from a cycloaliphatic hydrocarbon which is optionally substituted by 1 to 3 $(C_1–C_4)$ alkyl groups. Examples of suitable ketones of this type here are: methyl (iso)butyl ketone, methyl tert-butyl ketone, diisopropyl ketone, diisobutyl ketone, 5-methyl-3-heptanone, 4-heptyl ketone, cyclopentanone, cyclohexanone and 3,3,5-trimethylcyclohexanone.

The preferably aqueous crude mixture which is used according to the invention and which can be prepared by any desired route as a rule comprises at least 20% by weight, preferably at least 30% by weight and in particular at least 40% by weight, in each case with respect to the total mixture, of vinylphosphonic acid. In special cases, the proportion thereof can, however, also be less than 20% by weight.

Possible further constituents (impurities) are, in addition to water, in particular phosphoric acid, polyphosphoric acids and/or other phosphonic acid derivatives, such as, for example, hydroxyethanephosphonic acid, ethers of hydroxyethanephosphonic acid, esterification products of vinylphosphonic acid with hydroxyethanephosphonic acid and also mixed ethers and mixed esters of the individual compounds listed. The water concentration in the vinylphosphonic acid mixtures used can differ here, depending on the amount and type of the impurities contained in the crude vinylphosphonic acid.

The method according to the invention is expediently carried out at room temperature or at a moderately elevated temperature of up to about 90° C., preferably up to about 50° C., even higher temperatures, however, also being possible in principle, and in general under normal pressure. In special cases, the method can also be carried out under elevated or reduced pressure.

Suitable equipment for the extraction is the conventional industrial equipment, such as mixer-settler equipment or the conventional extraction columns with vibratory bases, rotating bases or fixed bases, or also simply pulsating packed columns in which the crude mixture and the extraction agent are fed in counter-current and in which the separation is carried out as fractionated extraction. The ratio of the feed amount of the crude mixture to the feed amount of the extraction agent is generally 1:1 to 1:20, preferably 1:2 to 1:10. Other ratios are also possible; these can easily be determined by a person skilled in the art and depend on the desired degree of extraction, on the extraction agent used and on the composition of the crude mixture.

In the case of the extraction according to the invention, in general only small amounts of impurities—usually phosphoric acid—pass into the extraction agent in addition to the vinylphosphonic acid. These impurities can be removed again by washing with a little water and the wash water can be recycled to the crude acid.

As a rule, a single extraction procedure in the separating column suffices to obtain a vinylphosphonic acid of the desired purity.

If necessary—if a highly pure, for example 99% pure vinylphosphonic acid is desired—this extraction separation can, however, be repeated after prior isolation of the vinylphosphonic acid and dissolving in water.

Working up of the vinylphosphonic acid solutions obtained according to the invention is possible in various ways. Thus, for example, the extraction agent can be distilled off from the dissolved vinylphosphonic acid, the vinylphosphonic acid then remaining as residue. However, the vinylphosphonic acid can also be back-extracted from the organic medium using water. The organic medium thus obtained can then be recycled directly in the cycle for the extraction of the vinylphosphonic acid from the crude mixture. The aqueous solution is evaporated; the residue is vinylphosphonic acid of the desired purity.

Since the extraction solution obtained according to the invention contains virtually exclusively vinylphosphonic acid, this extraction solution can be further processed directly, i.e. without intermediate isolation of the vinylphosphonic acid, for a number of further reactions of the vinylphosphonic acid, for example for polymerization in order to prepare polyvinylphosphonic acid or for copolymerization.

It was to be expected that the other phosphonic acid derivatives comprised in the mixture would display solubility characteristics similar to those of vinylphosphonic acid and would therefore not be able to be separated off by the extraction described. It was therefore not foreseeable, and is to be regarded as surprising, that vinylphosphonic acid in high purity of usually more than 85%, preferably 90 to 95%, and yields of usually more than 80%, preferably more than 85%, is obtainable from highly contaminated crude mixtures by the method according to the invention using special extraction agents, especially since a number of other conventional extraction agents give only unsatisfactory results. This applies, for example, to alcohols, such as butanol, esters, such as butyl acetate, ethers, such as diethyl ether, diisobutyl ether and dibutyl ether, or carboxylic acids, such as hexanoic acid.

Figure 1:
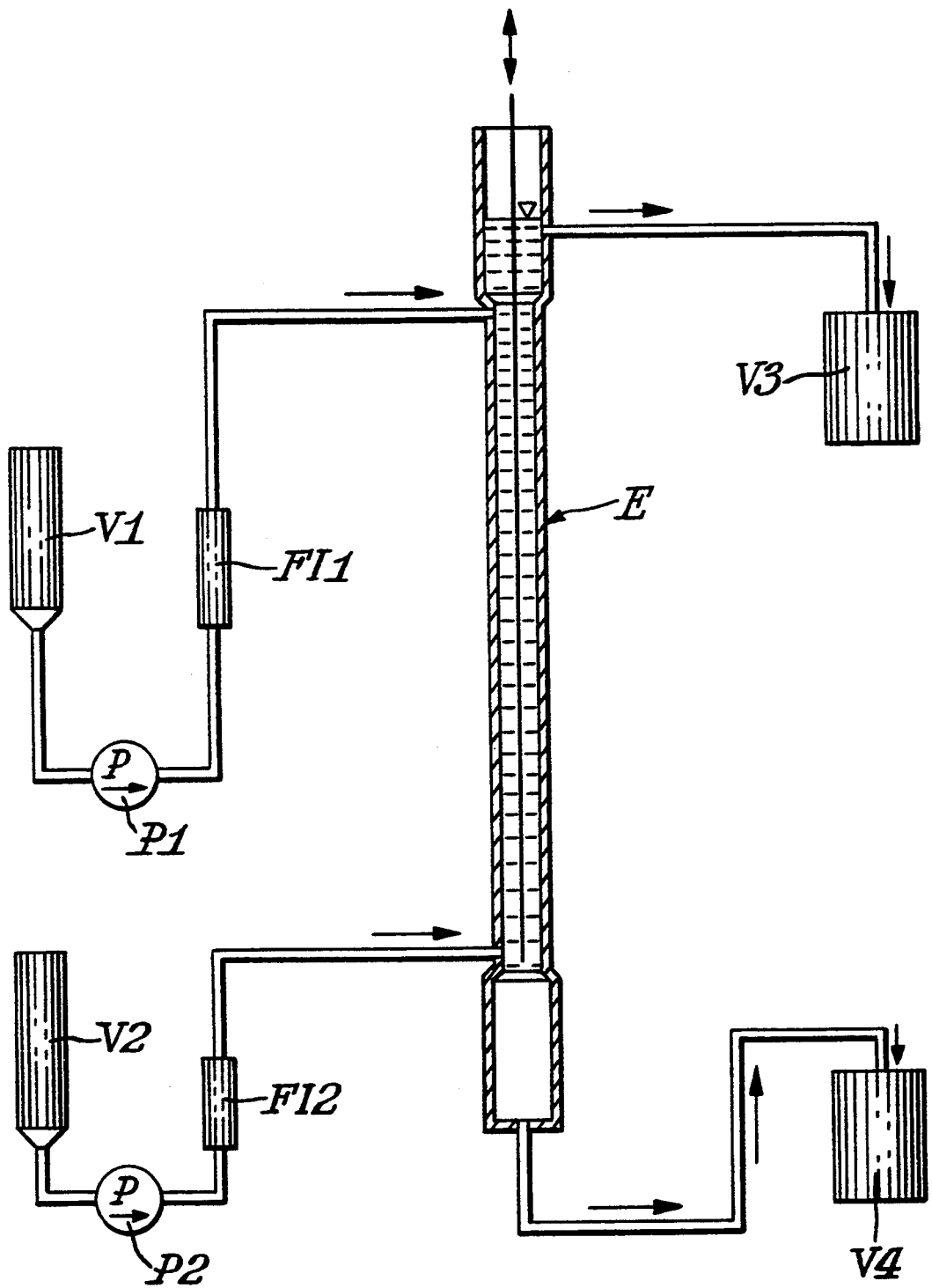
FIG. 1 shows the apparatus contemplated for carrying out the separation process.

The invention is illustrated by the following examples.

EXAMPLE 1

In an extraction column E in accordance with the appended FIG. 1 (internal diameter 25 mm, L=2 m, 35 trays, lift/thrust, frequency 60/minute), ethylhexanol was pumped in from vessel V2 via pump P2 and the flow meter F12 into the extractor E from below. After the extractor had been filled up to the overflow to vessel V3, pumping in of crude aqueous vinylphosphonic acid solution from the storage vessel V1 via pump P1 and the flow meter F11 into the upper part of the extractor E was started. After a heavy aqueous phase had collected in the lower separator vessel of extractor E, stripping of the aqueous phase to vessel V4 was started keeping the phase boundary of the aqueous phase constant. After running under constant conditions for several hours in order to establish the equilibrium, balancing was started. The following figures were established:

| | |
|---|---|
| Feed of 2-ethylhexanol from vessel V2 | 1.9 kg/h |
| Feed of crude vinylphosphonic acid from vessel V1 | 0.5 kg/h |

Composition of the crude vinylphosphonic acid, % by weight, which was obtained by hydrolysis of a thermally after-treated bottom product from the vacuum cleavage of dimethyl acetoxyethanephosphonate:

| | |
|---|---|
| Water | 40.3 |
| Vinylphosphonic acid | 40.7 |
| Phosphoric acid | 4.2 |
| Methoxyethanephosphonic acid | 6.1 |
| Vinylphosphonic acid esters of hydroxyethanephosphonic acid | 2.3 |
| Other phosphonic acids | 6.4 |

Downstream of the extractor 2.194 g/h of organic phase were obtained in vessel V3, whereas the amount of aqueous phase in vessel V2 was 206 g/h.

On evaporation of 2.194 g of the organic phase under vacuum, 188 g of residue were obtained. The residue comprised 91.4% by weight of vinylphosphonic acid. When the water content was calculated from the aqueous feed solution, calculation showed that a 91.4% pure vinylphosphonic acid is obtained as distillation residue in a yield, with respect to the feed, of 84.5% from a 68.2% pure vinylphosphonic acid in the feed.

EXAMPLE 2

The equipment and the experimental procedure corresponded to those of Example 1. However, the after-treatment of the organic phase was modified, 2.194 g of the organic phase being thoroughly stirred with 600 g of water. After phase separation, the aqueous phase was evaporated under vacuum. 112 g of a 90.5% pure vinylphosphonic acid remained as residue.

EXAMPLE 3

The equipment and the experimental procedure corresponded to those of Example 1, but 2.194 g of the organic phase were extracted by shaking with 20 g of water. After phase separation and stripping of the aqueous phase, the organic phase was stirred thoroughly once more with 600 g of water. After renewed phase separation, the aqueous phase was evaporated. 105 g of 97% pure vinylphosphonic acid remained as residue.

EXAMPLE 4

The procedure was as described in Example 3. However, after treatment of the organic phase with 20 g of water and phase separation the organic phase was evaporated under vacuum. 171 g of a 98% pure vinylphosphonic acid remained as residue.

EXAMPLE 5

A crude vinylphosphonic acid of the following composition was prepared by thermal decomposition of dimethyl acetoxyethanephosphonate under normal pressure analogously to German Offenlegungsschrift 3

001 894 and subsequent hydrolysis of the monomethyl vinylphosphonate mixture:

| | |
|---|---|
| Vinylphosponic acid | 73% by weight |
| Polyvinylphosphonic acid | 1% by weight |
| Methoxyethanephosphonic acid | 1% by weight |
| Hydroxyethanephosphonic acid | 3% by weight |
| Vinylphosphonic acid esters of hydroxyethanephosphonic acid | 6% by weight |
| Phosphoric acid | 11% by weight |
| Other phosphonic acids | 5% by weight |

This crude vinylphosphonic acid was mixed with water in a weight ratio of 1:1.

1.5 kg of the aqueous vinylphosphonic acid were introduced into the extractor E in the arrangement according to Example 1.

The extraction agent used was cyclohexanol; the feed per hour was 2.0 kg.

After evaporation of the organic phase downstream of the extractor under vacuum, 486 g/h of 90% pure vinylphosphonic acid remained as residue.

EXAMPLE 6

The test arrangement and amounts were as described in Example 1. However, instead of 2-ethylhexanol, methyl isobutyl ketone was used as extraction agent. After distilling off the methyl isobutyl ketone, 120 g/h of residue were obtained which contained 90% by weight of vinylphosphonic acid.

COMPARISON EXAMPLE A

The test arrangement and amounts were as described in Example 1. However, instead of 2-ethylhexanol, di-n-butyl ether was used as extraction agent. After evaporation of the organic phase downstream of the extractor, 6 g of residue remained, which contained 43% of vinylphosphonic acid.

COMPARISON EXAMPLE B

The procedure was as in comparison test A, except that butanol was used instead of di-n-butyl ether as extraction agent. After evaporation of the organic phase downstream of the extractor, 130 g of residue remained, which contained 69% by weight of vinylphosphonic acid.

COMPARISON EXAMPLE C

The di-n-butyl ether of comparison example A was replaced by butyl acetate. After evaporation of the organic phase downstream of the extractor, 20 g of residue were obtained, which contained 71% by weight of vinylphosphonic acid.

COMPARISON EXAMPLE D

The di-n-butyl ether of comparison example A was replaced by caproic acid. After evaporation of the organic phase downstream of the extractor 60 g of organic phase were obtained, which contained 75% of vinylphosphonic acid.

I claim:

1. A method for separating vinylphosphonic acid from a crude mixture containing said acid, comprising the step of effecting the separation by extraction with an alcohol extraction agent, a ketone extraction agent, or a mixture of said extraction agents, each said alcohol or ketone extraction agent comprising at least 5 carbon atoms.

2. The method as claimed in claim 1, wherein the extraction agent has 5 to 15 carbon atoms.

3. The method as claimed in claim 1, wherein the extraction agent used is saturated aliphatic or cycloaliphatic alcohol, ketone or mixture thereof.

4. The method as claimed in claim 1, wherein the extraction agent used is 2-ethylhexanol, cyclohexanol, methyl isobutyl ketone or a heptanol.

5. The method as claimed in claim 1, wherein the crude mixture comprises water and at least 20% by weight, weight, with respect to the total crude mixture, of vinylphosphonic acid.

6. The method as claimed in claim 1, wherein the extraction is carried out in a column in counter-current.

7. The method as claimed in claim 1, wherein the extraction is carried out at temperatures of 20 to 90° C.

8. The method as claimed in claim 6 wherein the ratio of feed amount of the crude mixture to the feed amount of the extraction agent to the column is 1:1 to 1:20.

9. The method as claimed in claim 1, wherein a vinylphosphonic acid solution is obtained as a result of said separation, and wherein the resulting vinylphosphonic acid solution is worked up by evaporation to give vinylphosphonic acid.

10. The method as claimed in claim 9, wherein the resulting vinylphosphonic acid solution is used for further reactions without isolation of the pure acid.

11. The method as claimed in claim 1, wherein the crude mixture comprises water and at least 30% by weight, with respect to the crude mixture, of vinylphosphonic acid.

12. The method as claimed in claim 8, wherein said ratio is 1:2 to 1:10.

13. A method for separating vinylphosphonic acid from a crude mixture containing vinylphosphonic acid and phosphoric acid, comprising the step of effecting the separation by extraction with an alcohol extraction agent, a ketone extraction agent, or a mixture of said extraction agents, each said alcohol or ketone extraction agent comprising at least 5 carbon atoms.

14. The method as claimed in claim 13, wherein the extraction agent has 5 to 15 carbon atoms.

15. The method as claimed in claim 13, wherein the extraction agent used is a saturated aliphatic or cycloaliphatic alcohol, ketone or a mixture thereof.

16. The method as claimed in claim 1, wherein the extraction agent used is 2-ethylhexanol, cyclohexanol, methyl isobutyl ketone or a heptanol.

17. The method as claimed in claim 13, wherein the crude mixture comprises water, phosphoric acid at least one other phosphonic acid besides vinylphosphonic acid or an ester of said other phosphonic acid, and at least 20% by weight, with respect to the total crude mixture, of vinylphosphonic acid.

18. The method as claimed in claim 17, wherein said crude mixture is obtained from the hydrolysis of a vinylphosphonic acid ester which has been obtained by vacuum cleavage of a dialkyl acetoxyethanephosphonate.

* * * * *